(12) United States Patent
Vial et al.

(10) Patent No.: US 11,035,909 B2
(45) Date of Patent: Jun. 15, 2021

(54) METHOD OF CALIBRATING A NETWORK OF MAGNETOMETERS

(71) Applicant: COMMISSARIAT À L'ÉNERGIE ATOMIQUE ET AUX ÉNERGIES ALTERNATIVES, Paris (FR)

(72) Inventors: Franck Vial, Grenoble (FR); Saifeddine Aloui, Grenoble (FR)

(73) Assignee: COMMISSARIAT À L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 14 days.

(21) Appl. No.: 16/381,298

(22) Filed: Apr. 11, 2019

(65) Prior Publication Data
US 2019/0317159 A1 Oct. 17, 2019

(30) Foreign Application Priority Data
Apr. 16, 2018 (FR) ...................... 1853319

(51) Int. Cl.
*G01R 33/00* (2006.01)
*G01V 3/08* (2006.01)

(52) U.S. Cl.
CPC ..... *G01R 33/0035* (2013.01); *G01R 33/0094* (2013.01); *G01V 3/081* (2013.01)

(58) Field of Classification Search
CPC . G01R 33/0035; G01R 33/0094; G01V 3/081
USPC ...................................................... 324/202
See application file for complete search history.

(56) References Cited

U.S. PATENT DOCUMENTS

| | | | |
|---|---|---|---|
| 7,133,793 B2 | 11/2006 | Ely et al. | |
| 2015/0168123 A1* | 6/2015 | Hautson | G01R 33/0094 702/150 |
| 2015/0301216 A1* | 10/2015 | Hautson | G01V 3/081 324/247 |
| 2018/0003777 A1* | 1/2018 | Sorensen | G01R 33/0206 |

FOREIGN PATENT DOCUMENTS

| | | |
|---|---|---|
| EP | 1184684 A2 | 3/2002 |
| FR | 2915568 A1 | 10/2008 |
| WO | 2014079740 A2 | 5/2014 |
| WO | 2018011492 A1 | 1/2018 |

OTHER PUBLICATIONS

Preliminary French Search Report for French Application No. 1853319 dated Jan. 15, 2019.

* cited by examiner

*Primary Examiner* — Christopher E Mahoney
(74) *Attorney, Agent, or Firm* — Pearne & Gordon LLP

(57) ABSTRACT

A method of calibrating a network of magnetometers (C1, Ci) including the displacement of a magnet holder tool (10) above the network, and solving an optimisation problem to determine a localisation of the magnetometers in the network. This localisation minimises based on an optimisation criterion, the difference between a real attribute (D, m1, m2) of the magnet holder tool and an estimate of the attribute determined without knowledge of the displacement, starting from the localisation and measurements made by the magnetometers in the network during the displacement.

14 Claims, 2 Drawing Sheets

METHOD OF CALIBRATING A NETWORK OF MAGNETOMETERS

CROSS-REFERENCE TO RELATED APPLICATIONS

This application claims priority from French Patent Application No. 1853319 filed on Apr. 16, 2018. The content of this application is incorporated herein by reference in its entirety.

TECHNICAL FIELD

The field of the invention is monitoring the movement of a moving magnetic object by means of a set of magnetometers arranged in a network. The invention more particularly relates to calibration of the magnetometers network to determine the positions and orientations the magnetometers in a coordinate system associated with the network.

STATE OF PRIOR ART

The movement of one or several magnetic objects can be monitored by a set of magnetometers fixed to the same mechanical support such that their relative positions and orientations are fixed in time. The magnetometers are thus arranged in a network, this network sometimes abusively being qualified as a matrix although the relative positions and orientations of the magnetometers are not necessarily in any regular order and the magnetometers are not necessary located in the same plane. For the purposes of this disclosure, a magnetometers network means any arrangement of static or alternating magnetic field sensors.

In order to estimate the parameters of the magnetic object such as its position and orientation in a coordinate system associated with the magnetometers network, typically a coordinate system fixed to the support carrying the magnetometers, we can make use of a positioning method that uses:
- a model to simulate the magnetic field radiated by the object at all points in space;
- measurements originating from the magnetometers in the network; and
- an algorithm capable of estimating the position and orientation of the magnetic object making use of the difference between expected measurements and observed measurements.

The use of such a method assumes that the positions and orientations of the magnetometers are known in advance in the network coordinate system. However, this knowledge can be incorrect due to manufacturing and/or network assembly tolerances, and due to magnetometer manufacturing tolerances (the real position and orientation of the measurement axes of a magnetometer are not generally given, or when they are given, it is with tolerances not better than the order of 500 µm and 1° respectively). Therefore it appears essential to calibrate the magnetometers in the network coordinate system (therefore post-manufacturing and post-assembly) before making use of the measurements to position the magnetic object sufficiently accurately.

As an example of a known calibration technique for a magnetometers network, mention may be made of document FR 2 915 568 B1 that discloses a method of calibrating sensitivities and orthogonality defects of measurement axes of one or several magnetometers by making rotations in a uniform magnetic field. The approach can be extended to include all magnetometers in a network provided that the magnetic field is homogeneous and uniform over the entire volume occupied by the network during the rotations. This technique can determine the orientations of magnetometers in the network. On the other hand, it cannot be used to obtain the position of magnetometers within the network.

Another example of a known technique for calibration of a magnetometers network is given in document U.S. Pat. No. 7,133,793 B2 that discloses the possibility of calibrating a panel of magnetometers (X-Y digitiser) designed to determine the XY position of a stylus type magnetic source. The calibration system is composed of a grid of field generators (coils) in position above the panel. The alignment of the grid with the panel is measured by imagery. The generators, the position of which in the grid is known, are activated sequentially. An algorithm compares known positions of generators with positions estimated by the panel, so as to generate a calibration map. This map is then used to correct the X, Y positioning offsets and non-linearities of the panel.

In this document U.S. Pat. No. 7,133,793 B2, the grid is used as a reference and therefore it must be perfectly made and/or characterised. Its mesh and its surface area must also be adapted to the surface area of the panel and the required spatial resolution. The calibration also requires a positioning imagery system and coil control electronics. Therefore this calibration technique appears to be complex and expensive, and furthermore it can only be used for 2D localisation.

PRESENTATION OF THE INVENTION

The purpose of the invention is to improve the precision of localisation (position and/or orientation) of a moving object by a network of magnetometers by disclosing a simple, fast and inexpensive method of collectively calibrating magnetometers in the network with minimal external equipment.

To achieve this, the invention discloses a method of calibrating a network of magnetometers comprising the following steps:
- acquisition of measurements made by the magnetometers in the network when a tool carrying at least two magnetic field sources is displaced over the network;
- reconstruction of a path of the magnetic field sources during the displacement, from the acquired measurements and for a possible localisation of the magnetometers in the network;
- calculation of an estimate of a tool attribute from the reconstructed path;
- comparison between the tool attribute and the calculated estimate of said attribute; and
- determination of a localisation of the magnetometers in the network from the result of the comparison step.

Some preferred but non-limitative aspects of this method are as follows:
- the reconstruction, calculation and comparison steps are reiterated for one or several other possible localisations of the magnetometers, the localisation determined during the determination step corresponding to a possible localisation for which the result of the comparison is less than a threshold or to the possible localisation for which the result of the comparison is minimal after a given number of reiterations;
- for each sampling instant of the acquired measurements, the reconstruction step comprises the evaluation of one or several possible characterisations of the magnetic field sources, the evaluation of one possible characterisation comprising the calculation of a difference between the acquired measurements and an estimate of the magnetic field generated at said possible localisation of the magnetometers by the magnetic field sources having said possible characterisation;

a possible characterisation of the magnetic field sources includes geometric and magnetic characteristics composed of positions and magnetic moments of the magnetic field sources;

the tool attribute is a distance between the magnetic field sources carried by the tool;

the tool attribute is an amplitude of the magnetic moment of each of the magnetic field sources;

the tool attribute is a relative orientation of the magnetic moments of each of the magnetic field sources;

the amplitude of the magnetic moment of each of the magnetic field sources is identical;

the tool comprises two magnetic field sources of which the magnetic moment direction vectors are oriented along opposite directions;

displacement of the tool comprises a plurality of static phases;

the tool is displaced manually by an operator;

the magnetometers network is composed of magnetometers belonging to a plurality of magnetometer structures associated with each other.

BRIEF DESCRIPTION OF THE DRAWINGS

Other aspects, purposes, advantages and characteristics of the invention will be better understood after reading the detailed description given below of preferred embodiments of the invention, given as non-limitative examples, with reference to the appended drawings on which.

DETAILED PRESENTATION OF PARTICULAR EMBODIMENTS

The invention relates to a method for collective calibration of magnetometers carried by a mechanical support and forming a network of magnetometers. The purpose of the calibration is to determine a localisation, in other words a position and/or an orientation, of each magnetometer forming the network, in a coordinate system associated with the network, for example a coordinate system having one of the magnetometers for its origin.

Figure 1:
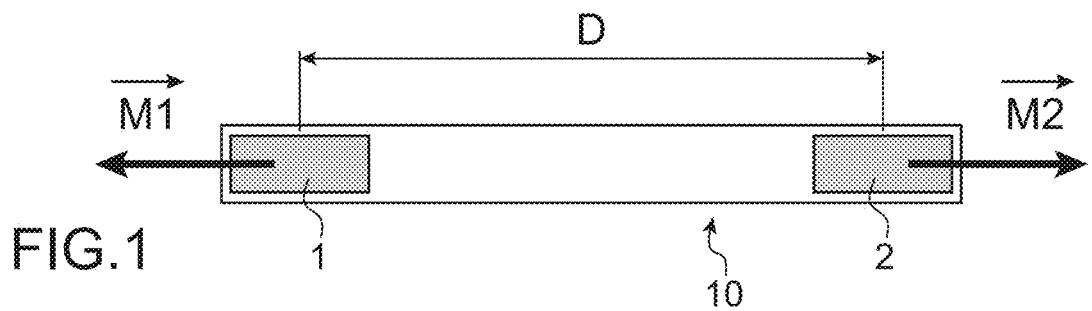
FIGS. 1 and 2 are diagrams representing two variants of a tool holding magnets that can be used in the context of the invention.
Figure 2:
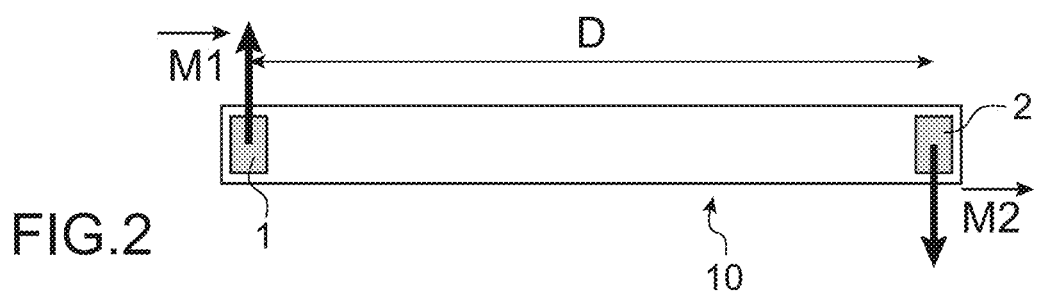

The calibration method according to the invention uses a tool carrying at least two magnetic field sources such as magnets or electromagnets, one attribute (in other words a characteristic or property) of which is known, for example a geometric or magnetic attribute. The following description uses the example of magnets and the tool is called a magnet holder. As shown on FIGS. 1 and 2, the magnet holder tool 10 can be in the form of a bar made of a non-magnetic material, for example aluminium, on which two magnets 1, 2 are fixed, typically with a magnet arranged at each end of the bar. Obviously, the magnet holder tool 10 could be in any other form such as a disk.

An example of a geometric attribute is the relative distance D between the centres of gravity of the magnets 1, 2. It is assumed that each of the magnets 1, 2 can be treated as a magnetic dipole, and is therefore at a point. Therefore to determine the relative distance D, in practice the dimensions of the magnets have to be known and the distance between the magnets has to be measured so that the distance between the two centres of gravity can be deduced.

An example of a magnetic attribute is the amplitude of the magnetic moments of each of the magnets. Another example of a magnetic attribute is the relative orientation of the magnetic moments of the magnets 1, 2.

Preferably, the amplitudes m1, m2 of the magnetic moments $\vec{M1}=m1\vec{u1}$, $\vec{M2}=m2\vec{u2}$ of the magnets 1, 2 are identical so as to limit magnetic masking effects between the magnets. Furthermore, the direction vectors $\vec{u1}$, $\vec{u2}$ of the magnetic moments $\vec{M1}$, $\vec{M2}$ of the magnets 1, 2 are preferably oriented along opposite directions so as to accentuate magnetic gradients at the magnetometers in the network and thus enrich the information. These direction vectors may for example be parallel to (FIG. 1) or orthogonal to (FIG. 2) the longitudinal axis of the bar.

The attributes of the magnet-holder tool 10, for example the amplitudes of the magnetic moments, the relative orientation of the magnetic moments and the relative distance D, are known with a precision level coherent with that of the expected calibration. For a fine calibration, the amplitude of the magnetic moments is known typically within 0.5%, their orientation within 1° and the distance D within 100 μm. Precisions better than 10%, 10° and 1 mm respectively are considered to be sufficient to lead to a qualitatively significant calibration.

The amplitude m1, m2 of the magnetic moment of the magnets 1, 2 that depends on the nature of the material and the volume of the magnets, is adapted to the resolution of the magnetometers in the network and the target range, for example 0.3 A·m$^2$ for displacement of the tool 10 a few centimetres above a network comprising magnetometers sensitive to a few hundred nano Teslas (0.3 A·m$^2$ corresponds to about 300 mm$^3$ of the neodymium-iron-boron magnetic material).

The distance D between the magnets is sufficient so that these two magnetic sources are separable with regard to the magnetometers. This distance can advantageously be reduced by positioning the magnets head to toe to generate strong local magnetic fields. Strictly, this distance D must not be less than the smallest distance separating two magnetometers in the network. This distance D is such that a projection of magnets 1, 2 onto the network, for example on a horizontal plane if the network is horizontal, is inscribed inside the area occupied by the set of magnetometers forming the network. Typically, it can be fixed at 10 cm for a movement at a distance of a few centimetres above magnetometers spaced for each other by a few centimetres and occupying the area of an A4 sheet.

If the height of the movement is too small and/or the magnetic moment is too strong with regard to the measurement range of the magnetometers, the magnetic field will be too strong therefore causing saturation of the magnetometers. Conversely, if the height is too large and/or the magnetic moment is too weak, the magnetic field will be too weak with regard to the measurement noise of the magnetometers. Thus, it will be understood that the height is chosen as a function of the magnetometer measurement performances and the magnetic moment of the magnets. In practice, the value of the field at the magnetometers closest to the magnets must typically be 300 to 3000 times stronger than their measurement noise.

Figure 5:
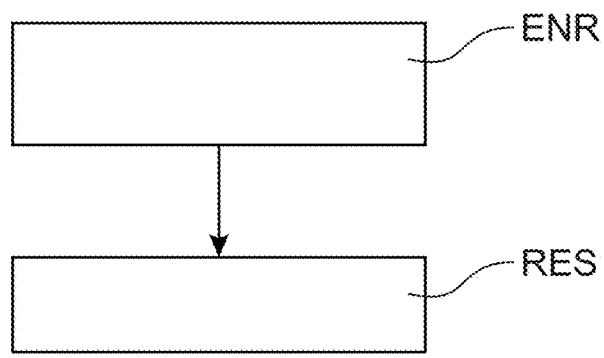
FIG. 5 is a flow chart showing the sequencing of the steps in the method according to the invention.

With reference to FIG. 5, the method according to the invention is broken down essentially into two phases: a first acquisition phase ENR of measurements made by magnetometers in the network during a displacement of the tool 10 above the magnetometers, and a second phase RES during which the acquired measurements will be processed. This method can be summarised as follows.

The magnet holder tool 10 is displaced above the magnetometers network, the magnetometers recording the variation of the distribution of the magnetic field and particularly the field generated by the magnet holder tool 10. At the same time, a model describes the magnetic behaviour of the magnets and predicts the spatial distribution of the magnetic field generated by the magnet holder 10. If the geometric and magnetic characteristics of the magnets are known, a prediction model can be produced as described below. By comparing effective measurements with predicted measurements, the position and the orientation of magnetometers in the network coordinate system can be estimated.

The example of a tool carrying two magnetic field sources 1, 2 is used in this case. However, the invention is not limited to this example and it covers a tool carrying more than two magnetic field sources, for example three magnets arranged to form a dihedron or even a matrix of magnets, which can be advantageous because the signals recorded by the magnetometers are then richer, with a better signal to noise ratio so that the number of measurements and therefore the recording duration can be reduced. The result is that there are then several distances and several angles (one to one distances and one to one angles). For example, magnets may be placed at the vertices of triangles, such that the angle between the magnetic moments is 277/3.

Acquisition Phase ENR

The tool 10 is displaced above the magnetometers each of which records the variation of the perceived magnetic field with time, during the displacement. This displacement may be made manually and at random by an operator. The entire surface of the network can thus be scanned at a potentially variable height and orientation of the tool. The signals are increasingly rich in information if the path is varied. The displacement heights of the two magnets are preferably similar to each other such that one magnet does not overshadow the other, the magnets generating a similar signal to noise ratio at the magnetometers. In other words, the tool 10 is displaced horizontally and preferably successively covering all parts forming the network of magnetometers in a horizontal plane parallel to the magnetometers network.

The displacement velocity must be compatible with the sampling frequency of the magnetometers, typically of the order of 1 cm/s for a sampling frequency of 100 Hz. In all, the displacement can thus last for several tens of seconds.

The displacement may also comprise a plurality of static phases, the tool remaining fixed for several seconds for different positions above the matrix. The recording then contains less information but the static phases make it possible to improve filtering of measurement noise. This can be done by successively placing the tool on the network in different positions that may or may not be predefined.

Processing Phase RES

This RES phase comprises the resolution of an optimisation problem to determine a localisation of magnetometers in the network. More particularly, said localisation minimises based on an optimisation criterion, the difference between a attribute of the tool 10 and an estimate of this attribute calculated without knowledge of the displacement, starting from said localisation and measurements acquired during the acquisition phase ENR.

Localisation that minimises the difference based on an optimisation criterion typically means a localisation associated with a difference less than a predetermined threshold or a localisation associated with a minimal difference after a maximum allowable number of iterations has been exceeded.

In one possible embodiment, the localisation determined by solution of the optimisation problem simultaneously comprises the positions and orientations of magnetometers in the network.

In another possible embodiment, the method comprises a preliminary step to determine the orientations of each of the magnetometers in the network, for example made according to the technique disclosed in document FR 2 9515 568 B1 discussed above. The localisation determined by solution of the optimisation problem then includes the positions of magnetometers in the network. This embodiment can reduce the number of degrees of freedom of the optimisation problem and thus avoid an incorrect calibration, particularly when the signal to noise ratio of the measurements is not good and/or when the measurements are not sufficiently reliable (for example due to a variable bias or non-linearities).

Solution of the optimisation problem includes an evaluation of a plurality of possible localisations of magnetometers in the network. Each evaluation of a possible localisation of magnetometers in the network comprises:
- starting from the possible localisation and acquired measurements, the calculation of an estimate of the attribute of the tool 10, without knowledge of the displacement, and
- the calculation of a difference between the attribute and the calculated estimate of said attribute.

As previously discussed, the known attribute of the magnet holder tool may include a distance D between magnets 1, 2 of the magnet tool holder 10. In addition or independently, the known attribute can include an amplitude of the magnetic moment of each of the magnets of the magnet holder tool, or their relative orientation. It will be noted that the estimate of the attribute can be helpful in identifying the magnets and therefore for example, to check that it is the right tool 10.

According to an approximation, each of the magnets 1, 2 of the magnet holder tool 10 can be treated like a point magnetic dipole. This approximation becomes valid if the distance between a magnetometer and the magnet is at least twice as large as the largest dimension of the magnet (for example its length for an elongated cylindrical magnet, or its diameter for a coin-shaped magnet). Magnetostatic laws can then be used to express the magnetic field at all points in space according to the following formula:

$$B(P, u, m) \text{ en } \mu T = \frac{m 10^{-1}}{d^5}(3 < u, P > P - d^2 u)$$

in which $$P = \begin{bmatrix} x \\ y \\ z \end{bmatrix}$$

the position of the magnet relative to the magnetometer;

$d=\|P\|$ the distance between the magnet and the magnetometer, such that $d^2=x^2+y^2+z^2$;

u is the direction vector of the magnetic moment of the magnet; and m is the amplitude of the magnetic moment of the magnet.

It will be noted that more detailed magnetic models, for example such as the Ampere model described in document WO 2017/005915 A1, can also be used to model the spatial distribution of the magnetic field generated by the two magnets 1, 2, particularly in the case in which the magnet passes very close to the magnetometers, since the dipole approximation is then no longer valid.

Figure 3:
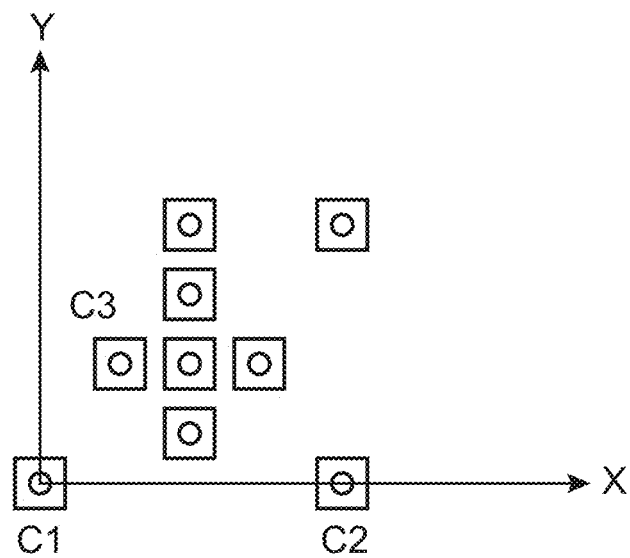
FIG. 3 is a diagram illustrating the definition of a coordinate system associated with the magnetometers network.

In this case the x, y, z coordinates are expressed in the coordinate system associated with the network. As shown on FIG. 3, this coordinate system can be obtained by choosing (for example arbitrarily), a first sensor C1 as the origin of the coordinate system, a second sensor C2 to define a first reference axis, and a third sensor C3 to define a second reference axis, such that these two reference axes are orthogonal. This third sensor C3 can define the direction of the second axis but it is not necessarily aligned on it. A third axis can be defined by means of a fourth sensor so as to obtain an orthogonal coordinate system in three dimensions for a non-plane magnetometers network.

Figure 4:
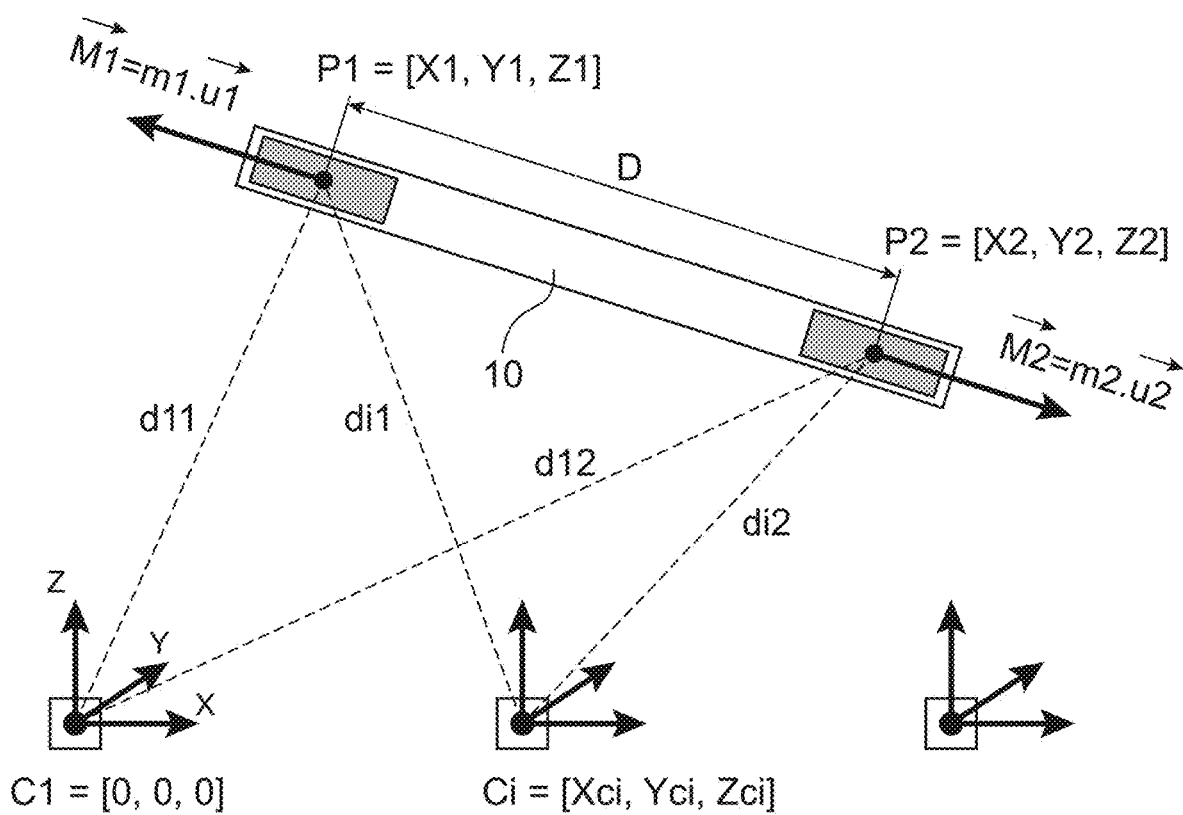
FIG. 4 represents a coordinate system associated with the network and the tool holding magnets, the coordinates of which are expressed in the coordinate system associated with the network.

FIG. 4 represents the magnet holder tool 10, the coordinates of which are expressed in the coordinate system associated with the network, with the sensor C1 as the origin. For a tool comprising two magnets, the field applied to each of the magnetometers is the sum of the fields generated by each of the two magnets. The field applied to sensor C1 is calculated as follows:

$$B_{C1} = \frac{m_1 \cdot 10^{-1}}{d_{11}^5}(3<u_1, P_1>P_1 - d_{11}^5 u_1) + \frac{m_2 \cdot 10^{-1}}{d_{12}^5}(3<u_2, P_2>P_2 - d_{12}^5 u_2),$$

in which $d_{11}=\|P_1\|$ and $d_{12}=\|P_2\|$.

The field applied to sensor Ci is expressed as follows:

$$B_{Ci} = \frac{m_1 \cdot 10^{-1}}{d_{i1}^5}(3<u_1, (C_i-P_1)>(C_i-P_1) - d_{i1}^5 u_1) +$$

$$\frac{m_2 \cdot 10^{-1}}{d_{i2}^5}(3<u_2, (C_i-P_2)>(C_i-P_2) - d_{i2}^5 u_2)$$

in which $d_{i1}=\|C_i-P_1\|$ and $d_{i2}=\|C_i-P_2\|$.

The distance D between the two magnets is calculated as $D=\|P_1-P_2\|$.

The calculated estimate of the tool attribute from measurements acquired during displacement of the magnet holder tool 20 depends on knowledge of the positions and orientations of the various magnetometers in the network. Thus an error in the knowledge of the positions and orientations of the magnetometers will lead to an error in the estimate of the attribute and therefore a difference between the real value of the attribute and its estimate.

Starting from a possible localisation of the magnetometers, it is thus possible to determine an error in estimating the attribute, for example an error in estimating the distance between magnets or an error in estimating the amplitude of the magnetic moment of each magnet. Thus, the invention can avoid the need for a coordinate system external to the network to estimate positioning errors of the magnetometers in the network and enable easily applied self-calibration making use of a magnet holder tool 10.

For each sampling instant, an error vector between known attributes and estimates of these attributes can thus be calculated. a denotes the vector of known attributes and â denotes the vector of estimated attributes for the possible localisation of the magnetometers. A quadratic error can be calculated on the set of n sampling instants using equation No. 1 below: $\epsilon = \Sigma_{i=1}^n(â(loc, [B_0 \ldots m_{-1}]_i)-a)^2$, in which loc is the vector containing the localisation parameters to be found (positions and possibly orientations of the magnetometers that remain fixed over time), and $[B_0 \ldots m_{-1}]_i$ is the vector of magnetic measurements made by magnetometers 0 to m−1 at sampling instant i.

Thus, to find vector loc, an attempt is made to solve the optimisation problem that consists of minimising this quadratic error according to equation No. 2:

$$loc = \text{argmin}_{loc} \Sigma_{i=1}^n (â(loc, [B_0 \ldots m_{-1}]_i)-a)^2.$$

Different optimisation algorithms can be used to minimise this function. For example, it is possible to use a gradient descent provided that it can be differentiated, in other words a variation of â can be calculated as a function of a variation of loc. In this case, the derivative is calculated numerically. It is also possible to use a genetic algorithm to overcome problems related to the variation calculation mentioned above. A hybrid algorithm using random mutations when there is a differentiability problem and a classical gradient descent if there are no differentiability problems may be preferred. Equation No. 2 may also be solved using a Kalman filter, a particle filter or a neurons network.

The vector â of estimated attributes for a possible localisation of magnetometers can be calculated in several steps. For example, if a applies to the distance D between magnets, a first step could consist of estimating the trajectory followed by the magnets during the displacement (the positions and magnetic moments of the two magnets at each instant i) using a similar optimisation technique: a search is made for positions and magnetic moments of magnets that minimise the error, for example quadratic, between magnetic field values measured at instant i and estimated values, fixing the positions and orientations of the magnetometers. Once the positions and magnetic moments of the magnets have been estimated for all instants i, the distance D is calculated using the formula given above. If the vector a applies to the norms of the two magnetic moments, the step mentioned above is performed and the norms are then deduced from the estimated values of moments (3D vectors). If the vector a applies to the relative orientation of the two magnets, the step mentioned above is performed, and the relative orientation is then estimated for example from the scalar product between the 2 direction vectors $\vec{u1}$ and $\vec{u2}$.

Thus, the estimation of the magnet holder attribute (i.e. calculation of the vector â for a possible localisation of the magnetometers) is preceded by a step to reconstruct a path followed by the magnets of the magnet holder tool during the displacement, for a possible location of magnetometers in the network.

This reconstruction step includes an evaluation of one or several possible characterisations of the magnets of the magnet holder tool, for each sampling instant of the acquired measurements. Characterisation of magnets refers particularly to the determination of geometric and magnetic characteristics of magnets composed of their positions and their magnetic moments.

The evaluation of a possible characterisation includes the calculation of a difference between the acquired measurements and an estimate of the magnetic field generated at said possible localisation of the magnetometers by magnets having said possible characterisation. The possible characterisation associated with the smallest difference is then used to calculate the estimate of the attribute for each sampling instant.

Therefore, globally, recursive optimisation is made with two stages: the first aims to estimate the trajectory of magnets during the displacement of the tool (the positions and magnetic moments of the magnets) for a given magnetometer location (to calculate a and the error E according to equation No. 1), the second aims to converge towards the positions and/or orientations of magnetometers that minimise the error according to equation No. 2. The first optimisation may be made using any of the algorithms, filters or networks mentioned above with reference to the second optimisation, without the means being used to make these two optimisations necessarily being identical. For example, a Kalman filter can be used for the first optimisation while a gradient descent algorithm can be used for the second optimisation.

Thus, the processing phase RES comprises:
a reconstruction of a path of the magnets in the magnet holder tool during the displacement, from the acquired measurements and for a possible localisation of magnetometers in the network;
a calculation of an estimate of a magnet holder tool attribute from the reconstructed path;
a comparison between the magnet holder tool attribute and the calculated estimate of said attribute; and
a determination of a localisation of magnetometers in the network from the result of the comparison.

The reconstruction, calculation and comparison steps are reiterated for one or several other possible localisations of the magnetometers until the result of the comparison step is less than a threshold. The possible localisation associated with this minimum value then forms the optimal localisation. Alternatively, the possible localisation is that which is associated with the minimum difference after a given number of iterations.

In all cases, it is preferred to initialise the algorithm with maximum a priori knowledge, such as the relative positions and orientations of the magnetometers (in general, their arrangement in the network is known by design), and their sensitivity (manufacturer data). The algorithm is thus initialised with realistic data that it will refine, which facilitates its convergence.

The calibration made by the invention is simple and fast. It does not require any large and expensive external equipment or instruments. A complete calibration of the magnetometers (position, orientation and sensitivity) can potentially be made in a single operation. The invention can then be used regardless of the distribution of the magnetometers, provided that this distribution remains fixed during and after the calibration (a priori knowledge of this distribution also being desirable to facilitate convergence of the localisation algorithm).

The invention can therefore also be used for systems with several magnetometer structures by expressing the coordinates of the set of magnetometers in a coordinate system associated with one of the structures used as reference. For example, such systems include 2D or 3D structures possibly but not necessarily contiguously adjoined, to extend the measurement volume, densify this capture volume or to change the geometry of the capture volume, for example such as plane structures that form a V arrangement. In such a case, the magnetometers network according to the invention is composed of the set of magnetometers in the different structures combined together.

The invention is not limited to the method as described above but also includes a magnetometry device comprising a network of magnetometers and a computer configured to implement this method and a computer program comprising instructions that, when the program is run on a computer, will effectively implement this method.

The invention claimed is:

1. A method for calibrating a network of magnetometers, comprising the steps of:
acquiring measurements made by the magnetometers of the network of magnetometers when a tool carrying at least two magnetic field sources is displaced over the network of magnetometers, the tool having a known tool attribute;
considering a possible localisation of the magnetometers in the network of magnetometers, reconstructing a path followed by the at least two magnetic field sources during displacement of the tool over the network of magnetometers, using the acquired measurements;
calculating an estimate of the known tool attribute from the reconstructed path;
comparing the known tool attribute and the calculated estimate of said known tool attribute; and
determining a localisation of the magnetometers in the network of magnetometers using the result of the comparing step.

2. The calibration method according to claim 1, in which the reconstructing, calculating and comparing steps are reiterated for one or several other possible localisations of the magnetometers, the localisation determined during the determining step corresponding to a possible localisation for which the result of the comparing step is less than a threshold or to a possible localisation for which the result of the comparing step is minimal after a given number of reiterations.

3. The calibration method according to claim 1, in which for each sampling instant of the acquired measurements, the reconstructing step comprises evaluating one or several possible characterisations of the at least two magnetic field sources, wherein evaluating a possible characterisation comprises calculating a difference between the acquired measurements and an estimate of the magnetic field generated at said possible localisation of the magnetometers by the at least two magnetic field sources having said possible characterisation.

4. The method according to claim 3, in which a possible characterisation of the at least two magnetic field sources includes positions and magnetic moments of the at least two magnetic field sources.

5. The calibration method according to claim 1, in which the known tool attribute is a distance between the at least two magnetic field sources.

6. The calibration method according to claim 1, in which the known tool attribute is an amplitude of a magnetic moment of each of the at least two magnetic field sources.

7. The calibration method according to claim 1, in which the known tool attribute is a relative orientation of magnetic moments of each of the at least two magnetic field sources of the tool.

8. The calibration method according to claim 1, in which an amplitude of a magnetic moment of each of the at least two magnetic field sources is identical.

9. The calibration method according to claim 1, in which the tool comprises two magnetic field sources of which magnetic moment direction vectors are oriented along opposite directions.

10. The calibration method according to claim 1, wherein the displacement of the tool comprises a plurality of static phases.

11. The method according to claim 1, in which the tool is displaced manually by an operator.

12. The method according to claim 1, in which the network of magnetometers is composed of magnetometers belonging to a plurality of magnetometer structures associated with each other.

13. A magnetometry device comprising a network of magnetometers and a computer configured to implement the calibration method according to claim 1.

14. A computer program comprising instructions which, when the program is run on a computer, cause the computer to implement the method according to claim 1.

* * * * *